US005577513A

United States Patent [19]

Van Vlasselaer

[11] Patent Number: 5,577,513

[45] Date of Patent: Nov. 26, 1996

[54] CENTRIFUGATION SYRINGE, SYSTEM AND METHOD

[75] Inventor: Peter Van Vlasselaer, Sunnyvale, Calif.

[73] Assignee: Activated Cell Therapy, Inc., Mountain View, Calif.

[21] Appl. No.: 298,882

[22] Filed: Aug. 31, 1994

[51] Int. Cl.[6] .......... A61B 5/00

[52] U.S. Cl. .......... 128/765; 128/770

[58] Field of Search .......... 128/763, 765, 128/770; 210/782

[56] References Cited

U.S. PATENT DOCUMENTS

| | | | |
|---|---|---|---|
| 3,441,205 | 4/1969 | Young, Jr. et al. . | |
| 3,513,976 | 5/1970 | James . | |
| 3,706,305 | 12/1972 | Berger et al. . | |
| 3,706,306 | 12/1972 | Berger et al. . | |
| 3,750,645 | 8/1973 | Bennett et al. . | |
| 3,849,072 | 11/1974 | Ayres . | |
| 3,937,211 | 2/1976 | Merten . | |
| 3,957,654 | 5/1976 | Ayres . | |
| 3,965,889 | 6/1976 | Sachs . | |
| 3,985,122 | 10/1976 | Topham . | |
| 4,001,122 | 1/1977 | Griffin . | |
| 4,020,831 | 5/1977 | Adler . | |
| 4,022,576 | 5/1977 | Parker . | |
| 4,040,959 | 8/1977 | Berman et al. | 210/78 |
| 4,055,501 | 10/1977 | Cornell | 210/516 |
| 4,066,414 | 1/1978 | Selby | 23/259 |
| 4,112,924 | 9/1978 | Ferrara et al. . | |
| 4,134,512 | 1/1979 | Nugent | 215/247 |
| 4,147,628 | 4/1979 | Bennett et al. | 210/83 |
| 4,152,270 | 5/1979 | Cornell | 210/516 |
| 4,181,700 | 1/1980 | Chervenka et al. | 422/102 |
| 4,213,456 | 7/1980 | Böttger . | |
| 4,256,120 | 3/1981 | Finley | 128/764 |
| 4,373,535 | 2/1983 | Martell | 128/765 |
| 4,378,812 | 4/1983 | Sarstedt | 128/765 |
| 4,443,345 | 4/1984 | Wells | 210/782 |
| 4,459,997 | 7/1984 | Sarstedt | 128/764 |
| 4,511,349 | 4/1985 | Nielsen et al. | 494/16 |
| 4,562,844 | 1/1986 | Carpenter et al. | 128/675 |
| 4,569,764 | 2/1986 | Satchell | 210/511 |
| 4,588,556 | 5/1986 | Sarstedt | 422/101 |
| 4,610,846 | 9/1986 | Martin | 422/101 |
| 4,707,276 | 11/1987 | Dodge | 210/789 |
| 4,774,963 | 10/1988 | Ichikawa et al. | 128/763 |
| 4,824,560 | 4/1989 | Alspector . | |
| 4,828,716 | 5/1989 | McEwen et al. | 210/740 |
| 4,844,818 | 7/1989 | Smith | 210/789 |
| 4,886,071 | 12/1989 | Mehl et al. | 128/760 |
| 4,917,801 | 4/1990 | Luderer et al. | 210/516 |
| 4,954,264 | 9/1990 | Smith | 210/767 |
| 4,957,638 | 9/1990 | Smith | 210/782 |
| 5,030,341 | 7/1991 | McEwen et al. | 210/94 |
| 5,039,401 | 8/1991 | Columbus et al. | 210/117 |
| 5,053,134 | 10/1991 | Luderer et al. | 210/516 |
| 5,132,232 | 7/1992 | Parker | 436/177 |
| 5,236,604 | 8/1993 | Fiehler | 210/782 |
| 5,248,480 | 9/1993 | Greenfield et al. | 422/68.1 |
| 5,269,927 | 12/1993 | Fiehler | 210/516 |
| 5,271,852 | 12/1993 | Luoma, II | 210/789 |
| 5,308,506 | 5/1994 | McEwen et al. | 210/745 |

FOREIGN PATENT DOCUMENTS

| | | |
|---|---|---|
| 0595641A2 | 10/1993 | European Pat. Off. . |
| 2556096 | 6/1985 | France . |

*Primary Examiner*—Max Hindenburg
*Attorney, Agent, or Firm*—Carol A. Stratford; Peter J. Dehlinger

[57] ABSTRACT

A centrifuge syringe for separating components of a fluid sample having different sedimentation densities is disclosed. The centrifuge syringe allows for the withdrawal of a sample through a sterile needle into the syringe. The syringe contains a movable plunger containing a restriction and which may contain a density gradient separation solution. The plunger is connected to a handle which is detachable to allow centrifugation. After centrifugation, the handle is reattached to the plunger, and the specimen is removed from the syringe.

35 Claims, 6 Drawing Sheets

CENTRIFUGATION SYRINGE, SYSTEM AND METHOD

BACKGROUND OF THE INVENTION

The present invention relates to the field of centrifugation in general, and more particularly to centrifuge tubes that also function as syringes.

The prior art contains numerous devices that provide for the extraction of fluid samples as well as their centrifugation. For example, U.S. Pat. No. 4,459,997 to Sarstedt discloses a blood extraction and centrifugation device that provides for the withdrawal of blood from a patient into a tube that can be used for centrifugation. The centrifugation tube is a simple straight-walled tube that does not contain a constricted region or provide for the use of density gradient material.

U.S. Pat. No. 4,020,831 to Adler discloses a syringe that can draw a specimen, and then allow disassembling of certain parts of the syringe so that the portion of the syringe holding the specimen can be placed in a centrifuge. The syringe also contains a plug of a specific density. During centrifugation, the specimen will separate so that lighter phases are above the plug, and heavier phases are below the plug. This device does not provide for easy removal of the separated phases, and does not provide for the use of a density gradient material.

In addition, U.S. Pat. No. 3,965,889 to Sachs discloses an apparatus for the sampling of blood and the separation of plasma. The syringe includes a thermosealable walled container with a medial restriction into which blood is drawn. After the blood is drawn into the container, the container is removed and placed in a carrier for centrifugation, after which the container can be sealed at the restriction to separate the phases of blood. This device requires the removal of the specimen container to a different carrier for centrifugation, thereby increasing the risk of contamination of the specimen.

There is thus a need in the art for a syringe that can be used to separate materials of different densities which is an integrated unit that does not require transfer of sample to a different container for centrifugation and therefore reduced risk of contamination. The present invention provides a sterile environment in which all required cell sorting manipulations can be carried out.

SUMMARY OF THE INVENTION

The present invention solves the above-stated needs by providing a centrifuge syringe that provides an integral syringe and centrifugation tube in one apparatus and further provides for the use of density gradient material to enhance the separation capabilities. The apparatus has a specimen container with one end having a fitting covering an orifice adapted for the sterile introduction or ejection of fluids, and the opposite end having a central orifice for the sealing engagement with a handle of a plunger. The handle is connected to a plunger at one end, which is located within the container. The opposite end of the handle remains outside the specimen container, and is used to move the plunger longitudinally within the container.

The present invention is specially adapted for use with a density gradient material for enhanced cell separation. The density gradient material is placed in the plunger of the container before the addition of the specimen to be centrifuged. The plunger has a bottom wall attached to the handle, and a top wall with a restriction, creating a fluid receiving area between the two walls. The use of a restriction in the top wall further aids in cell separation, and reduces the possibility that the separated phases will mix during collection of the phases after centrifugation.

The apparatus is also specially designed to allow the detachment of a needle or other sterile connecting device and the handle before centrifugation of the specimen. The handle may then be reattached to facilitate the removal of the specimen. Removal of the specimen can be easily accomplished by ejecting the low density phase, which reduces the possibility of contamination of the sample. Preferably the ejecting will be done with the syringe in an inverted position.

Further aspects of the invention include a closed system for centrifuge fluid analysis wherein the syringe according to the invention is used to draw a previously collected sample from a sterile container. Methods for separating cells utilizing the above describe syringe also form further aspects of the invention.

DESCRIPTION OF THE PREFERRED EMBODIMENTS

Figure 1:
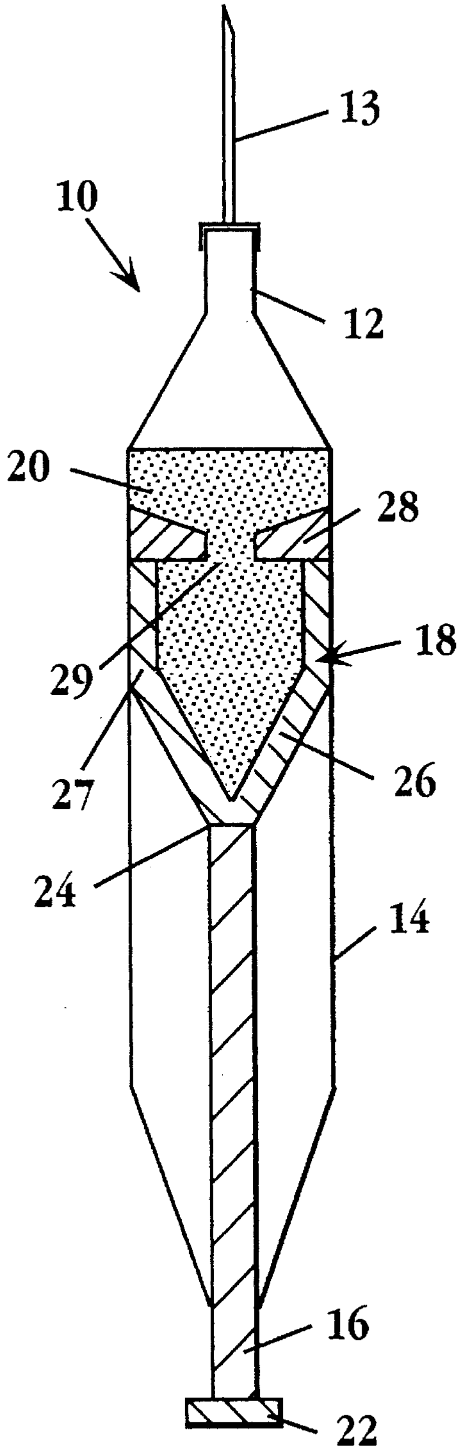
FIG. 1 is a cross-sectional view of a centrifuge syringe according to the invention before the extraction of a specimen.

One embodiment of centrifuge syringe 10 according to the invention is illustrated in FIG. 1. The centrifuge syringe 10 includes a specimen container 14 with a central orifice surrounded by fitting 12 adapted for receiving a needle 13, a handle 16 and a plunger 18. Fitting 12 may be any type of locking tip adapted to hold a needle, for example, a Luer-Lock™ syringe tip. Alternatively, fitting 12 may be a sterile septum adapted for connection with sterile fluid bags and tubes, for example a SAFSITE™ small wire extension set with reflux valve and Spin-Lock™ adaptor available from Burron Medical Inc., Bethlehem, Pa.

Handle 16 further preferably comprises knob 22 and a removable connection 24 to plunger 18. As shown in FIGS. 1–4, plunger 18 is single piece, machined or molded from a plastic material. Known medical grade plastic materials may be used. The plunger as shown in FIG. 1 has a funnel-shaped bottom wall 26 that is removably connected to the handle at connection 24. Side wall 27 preferably closely matches the container wall to permit sliding movement but provide an essentially fluid-tight barrier therearound. A top wall is formed by constriction member 28, which defines central opening 29. Alternatively, the outer diameter of side wall 27 may be slightly undersized to facilitate sliding and an o-ring seal provided between side wall 27 and container 14. Removable connection 24 may take the form of, for example, a screw fitting or a snap-fit. Preferably, connection 24 also provides for reattachment of handle 16. If reattachment is not desired, connector 24 may be designed such that handle 16 can be broken off. A suitable connection can be selected by those of ordinary skill in the art.

The plunger 18 is filled with a density gradient material 20 before the introduction of a specimen. As is understood by persons of ordinary skill in the art, such materials have specifically defined densities which are selected based on the particular sample material being separated. Examples of density gradient materials include sucrose, albumin and Ficoll™. A preferred material is available from Pharmacia Fine Chemicals of Piscataway, N.J. and Uppsala, Sweden under the trademark PERCOLL™. Preferably, the density gradient material is filled to a level above the constriction member, or at least above the top of opening 29. For example, when using a standard 50 ml syringe, having an inner diameter of about 2.8 cm, the gradient material is preferably filled to a level about 1 mm or more above constriction member 28. This fill level will help to prevent the formation of an interface portion, as explained below, under constriction member 28.

Figure 2:
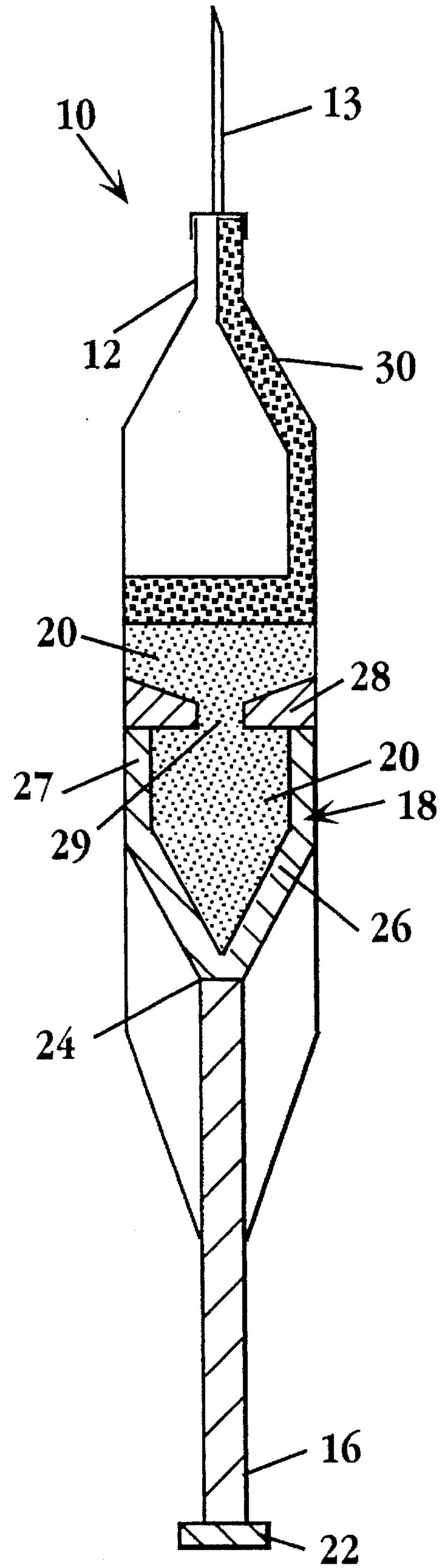
FIG. 2 is a cross-sectional view of the centrifuge syringe of FIG. 1 upon introduction of the specimen.

Referring to FIG. 2, the introduction of the specimen into centrifuge syringe 10 is illustrated. Specimen 30 is drawn into the syringe through needle 13 secured to fitting 12, aided by the vacuum created by handle 16 and plunger 18 as the handle is pulled out of container 14, drawing the plunger away from fitting 12. The handle should be pulled with sufficiently low force and velocity to avoid mixing of the specimen with the density gradient material onto which the sample is layered. Preferably, when the handle is pulled at an appropriate force, the sample will form a stream which adheres to the side of the container as it is drawn in, as shown in FIG. 2. This will reduce unwanted mixing. Mixing of the two materials is also minimized by the fact that the density of the specimen is significantly lower than the density of the density gradient material. After specimen 30 is drawn into container 14, the container is maintained in an upright position and the sample lies on top of density gradient material 20.

Figure 12:
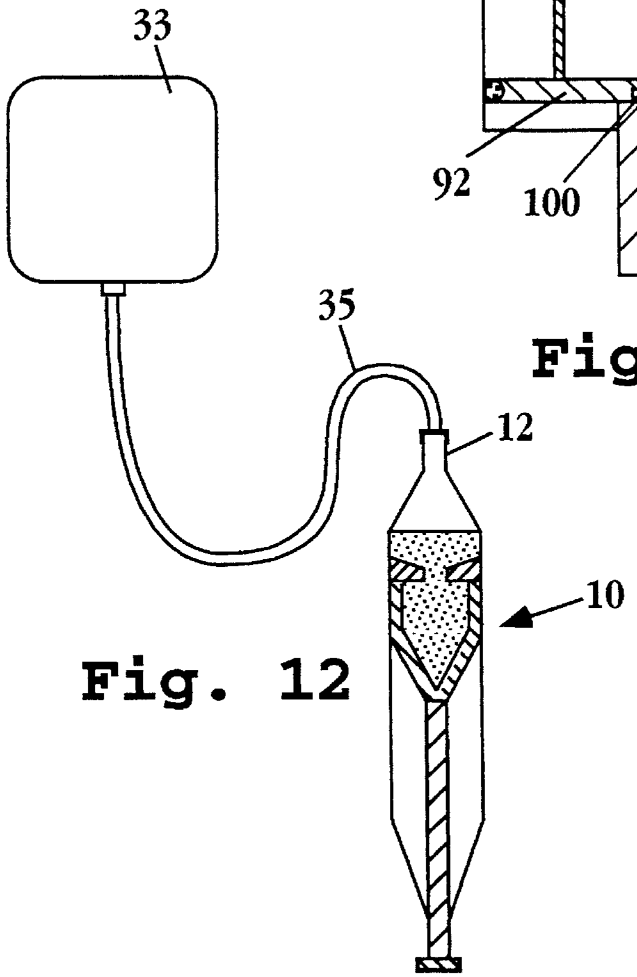
FIG. 12 is diagrammatic illustration of a closed system for blood analysis according to the present invention.

Using needle 13, a sample such as peripheral blood may be drawn directly from a patient for analysis. The present invention thus ensures sterility of such a sample by completely eliminating direct handling of the sample prior to introduction into the centrifugation container. Alternatively, as illustrated in FIG. 12, using a sterile septum as fitting 12, blood previously collected by known techniques and stored, for example in a sterile bag 33, may be drawn into the centrifugation container through sterile tubing 35 or other known sterile connection means. The present invention thus ensures a sterile transfer of sample material on a larger scale in a completely closed system, again without direct handling of sample material.

Once the specimen has been completely drawn into the container 14, and the handle 16 has been pulled so that the removable connection 24 is located at the central orifice of the specimen container 14, the handle 16 can be removed for the centrifugation step.

Figure 3:
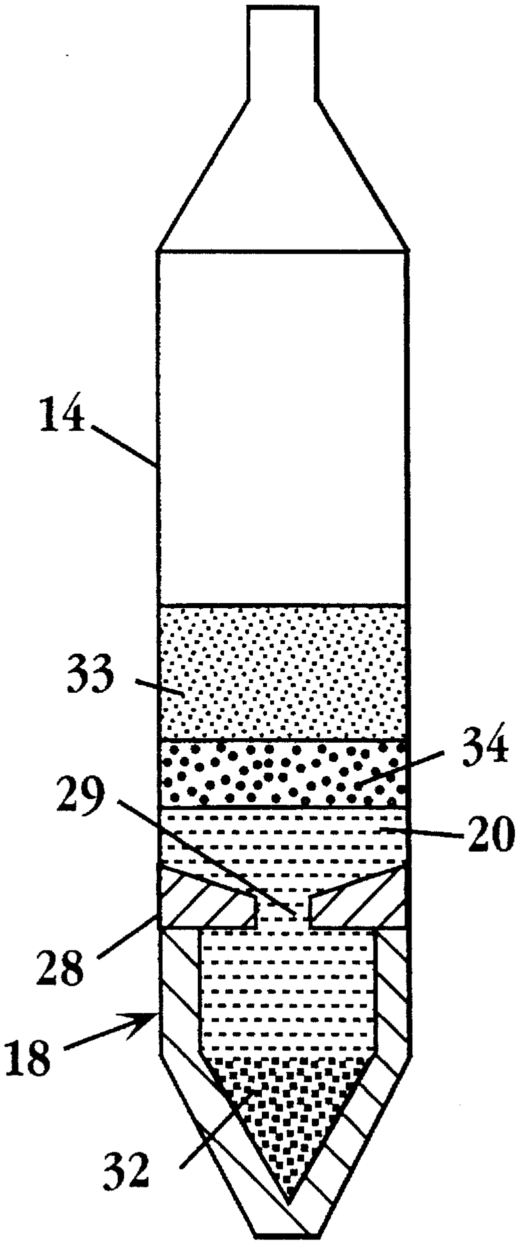
FIG. 3 is a cross-sectional view of the centrifuge syringe of FIG. 1 after centrifugation.

FIG. 3 illustrates the centrifugation syringe after the centrifugation step has been performed. As shown, the handle 16 has been detached from the plunger 18, which is located at the bottom end of the container 14. Centrifugation of container 14 results in a pellet 32 being formed from the heavier portions of the specimen at the bottom of the plunger 18. Density gradient material 20 is located above pellet 32. An interface portion 34, which contains the cells of interest, is formed between specimen diluent 33 and density gradient material 20, and above constriction member 28.

Figure 4:
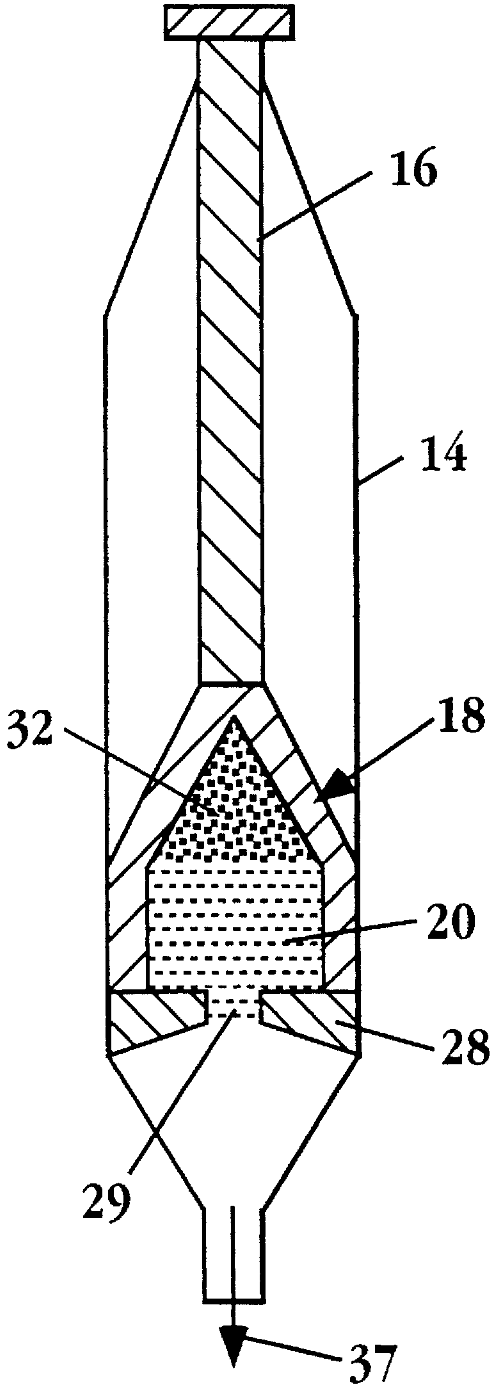
FIG. 4 is a cross-sectional view of the centrifuge syringe of FIG. 1 upon removal of the specimen.

Interface portion 34 may be removed from the centrifuge syringe 10 by inverting the centrifuge syringe and ejecting it off as indicated by arrow 37 in FIG. 4. Further removal of density gradient material 20 and the pellet 32 can be facilitated by reattaching handle 16 to plunger 18 at connection 24. The handle then can be pushed into the container to aid the removal of the material if necessary.

According to one theory, the presence of the constriction member with a restricted opening provides a support or nucleus for formation of an intermediate surface tension across the tube. This surface tension impedes the mixing of upper and lower regions (above and below the constriction member) of the tube when, for example, the contents of the upper region are ejected from the tube. Accordingly, the dimensions of the opening of the plunger are dictated by the ability to form a surface tension. A constriction member that is little more than a rim around the interior of the barrel may be sufficient to form the necessary surface tension. Hence, the cross-sectional area of the opening formed by the constriction member may be as little as about 5% or as great as about 95% of the horizontal cross-sectional surface area of the syringe. In an exemplary embodiment, where the syringe has an inside diameter of about 2.8 cm, an aperture having a diameter of about 0.5 cm is suitable.

In many applications, it will be desirable to collect only the supernatant fraction containing interface portion 34. In such cases, the pellet is discarded with the syringe. In other cases, the pellet can be removed by mechanical manipulation/disruption. For example, the syringe can be inverted and subjected to vortex mixing. Such mixing will disrupt the pellet into the adjacent liquid phase and will induce movement of this liquid phase and disrupted cells from the second or collection chamber of the syringe into the first chamber of the syringe.

Figure 5:
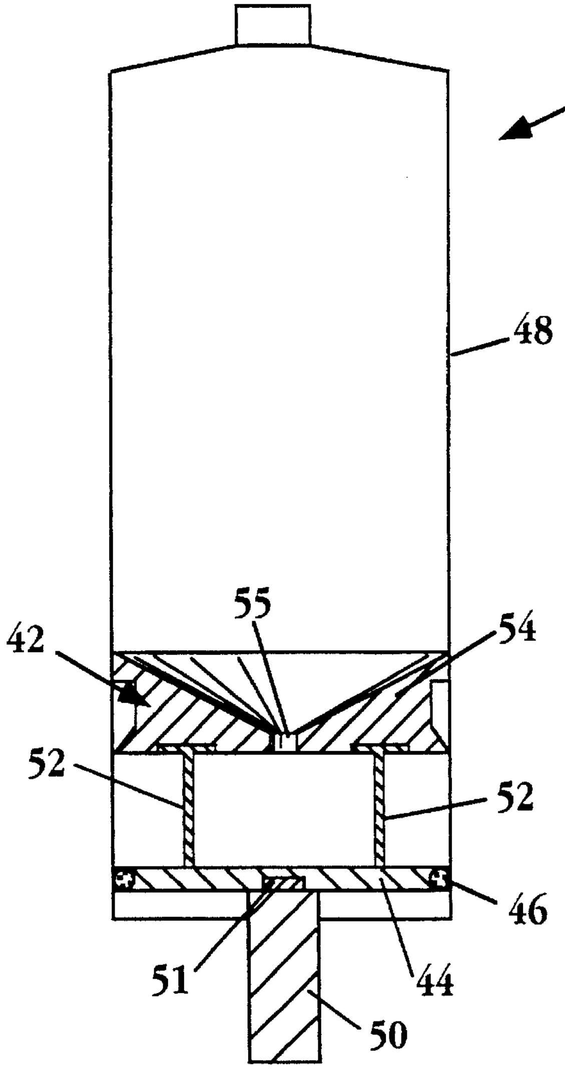
FIG. 5 is a cross-sectional view of an alternative embodiment of the centrifuge syringe according to the invention.
Figure 6:
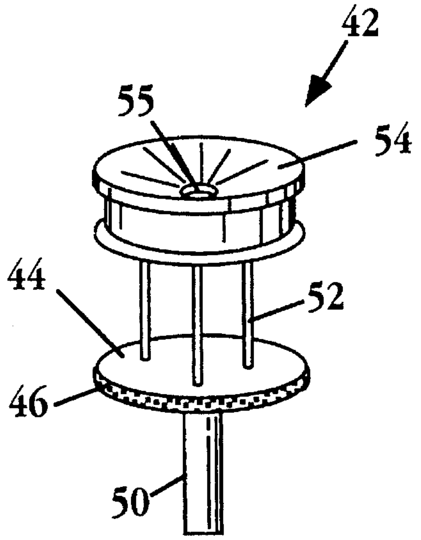
FIG. 6 is a perspective view of the plunger of the alternative embodiment of FIG. 5.
Figure 7:
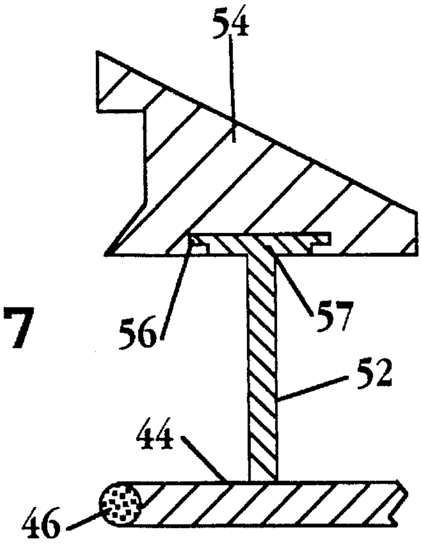
FIG. 7 is a cross-sectional view of the plunger through line 7—7 of FIG. 5.

An alternative embodiment of the present invention is shown in FIGS. 5–7. Centrifuge syringe 40 has a plunger 42 formed from separate pieces and without sidewalls. Plunger 42 has a flat bottom plate 44, which may be formed by a washer formed from medical grade plastic such as polycarbonate. Bottom plate 44 is preferably circumscribed by a silicone or rubber seal 46 for the creation of an fluid-tight seal between bottom plate 44 and the inside wall of the specimen container 48. Threaded or snap-fit connection 51 is provided in the bottom plate to removably attach handle 50. Plunger 42 has fittings 52, to connect bottom plate 44 to annular constriction member 54, which defines opening 55. Fittings 52 are preferably made of medical grade plastic, such as polycarbonate. Constriction member 54 is funnel-shaped, and preferably made of silicone or rubber. There are preferably three fittings 52, as shown, but there may be only two, or more than three if desired. The constriction member can be secured to the fittings by providing stepped recesses 56 in the constriction member, as shown in FIG. 7, for retaining mushroom like-heads 57 on the fittings. Fittings 52 may be glued to bottom plate 44 preferably with medical grade adhesive. Other means for connection may be devised by persons skilled in the art and the particular type of connection used is not critical so long as a secure connection between the parts is maintained.

An advantage of the present invention is that the low density material above the constriction member of the plunger is separated from material beneath by the simple act of, ejecting it with the aid of the plunger, as described above. If the opening at fitting 12 is large enough, the cells of interest may be poured off. This contrasts with many conventional methods of unloading gradient separations using standard straight-wall centrifuge tubes, where materials are separated by carefully pipetting out of the tube or, alternatively, by puncturing the bottom of the tube and allowing the contents of the tube to slowly drip out into collection vessels. Thus, the present invention provides a convenient, simple means for unloading differentially separated materials. In addition, unlike conventional straight-wall tubes, if the centrifuge syringe is dropped or accidentally inverted, the contents will not readily mix due to the presence of the constriction member. Moreover, once separation has taken place, the solution present above the constriction member can be mixed in the tube, without disturbing (or fear of contamination by) the contents of the syringe below the constriction member. Preferably this is done with the syringe in an inverted position as shown in FIG. 4.

Figure 8:
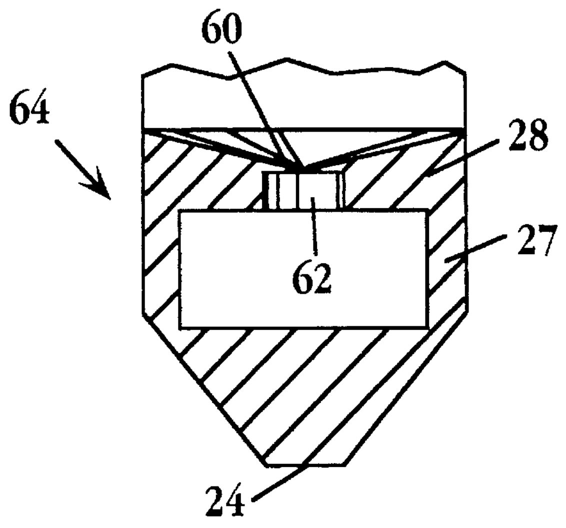
FIG. 8 is a cross-sectional view of an alternative embodiment of the centrifuge syringe plunger having a valve.
Figure 9A:
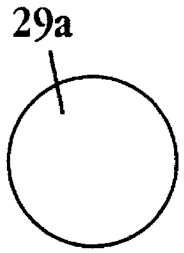
FIGS. 9A–9E are examples of the shape of the opening of the constriction member in the centrifuge syringe.
Figure 9B:
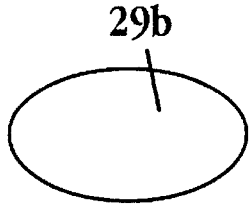
Figure 9C:
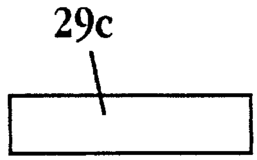
Figure 9D:
Figure 9E:
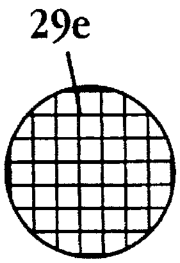

The separation of materials may be further enhanced by the addition of valve 60 to the plunger, as shown in FIG. 8. The valve 60 is located at opening 62 in plunger 64. Valve 60 may be a one-way valve, or a valve that only opens upon application of a threshold centrifugal force. The valve can be formed by providing flaps of a softer material over hole 62. In a preferred embodiment, the force required to open valve 60 would be about 850 times the normal force of gravity. Valve 60 thus allows heavy cells to pass through during initial centrifugation, and then keeps those cells in place, allowing for further processing, such as washing or mixing, of the lighter cells of interest located above the valve. In this way complete and final manipulation of the cells can be performed in a single sterile container.

The shape of opening 29, 55 is not limited to a circular shape, though in general a funnel-shaped constriction member forming a roughly circular shape 29A will be preferred. As shown in FIGS. 9A–E, the opening may also be oval 29B, rectangular 29C, star-shaped 29D, covered by a grid or mesh 29E or any other shape that would create a restricted opening.

Figure 10A:
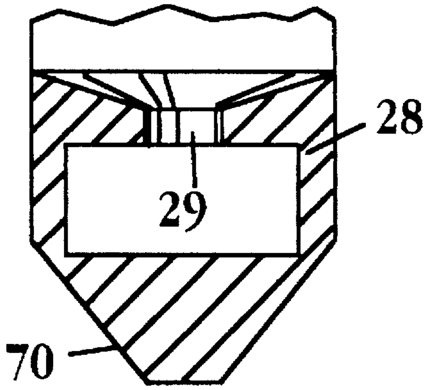
FIGS. 10A–10F are cross-sectional views of alternative embodiments of the plunger of the centrifuge syringe.
Figure 10B:
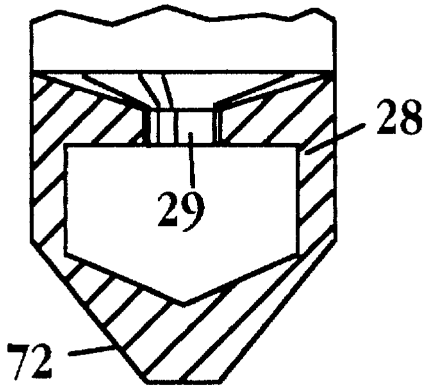
Figure 10C:
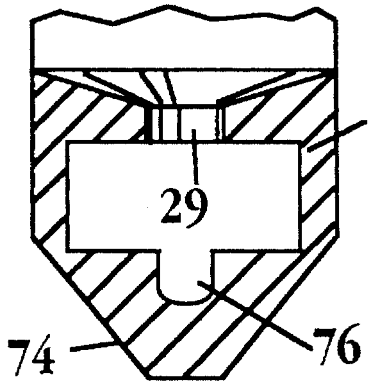
Figure 10D:
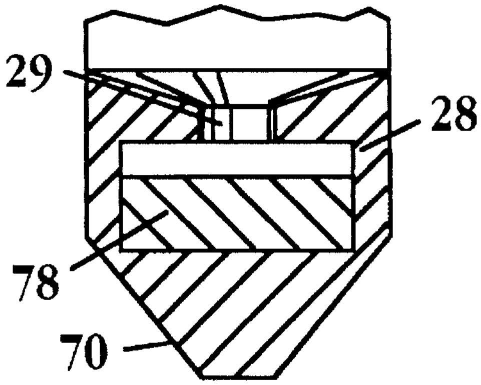
Figure 10E:
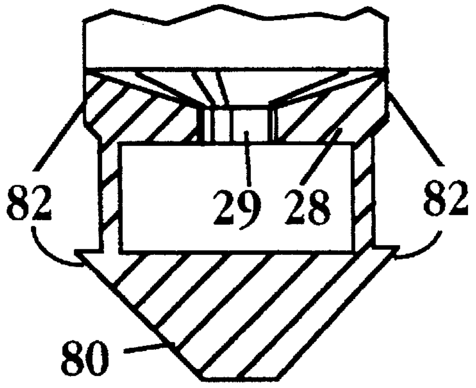
Figure 10F:
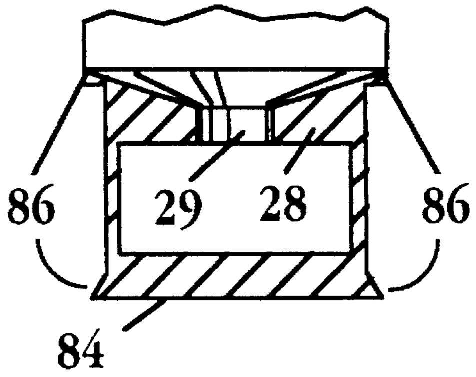

FIGS. 10A–F are illustrations of alternative shapes and designs for the plunger of the centrifuge syringe according to the invention. FIG. 10A shows a plunger 70 with a flat bottom wall. FIG. 10B shows a plunger 72 with a pointed bottom wall. Plunger 72 with the pointed bottom wall will allow the heavier cells to form a better pellet, which may be desired if the cells are to be collected. Alternatively, plunger 74 with a separate compartment 76 can be utilized to offer optimal collection of cells. FIG. 10D shows a plunger 70 that includes a cell trapping material 78, such as a sponge or gel. Material 78 may contain compounds that specifically bind certain cell types or toxins that kill specific cell types. Material 78 may also be made of a magnetic material if desired. FIGS. 10E and F show alternative embodiments of the plunger that facilitate movement within the container. FIG. 10E shows a plunger 80 with extending contact points 82. The plunger 80 will only contact the container at these points. Similarly, in FIG. 10F, a plunger 84 is shown with extending contact points 86.

Figure 11:
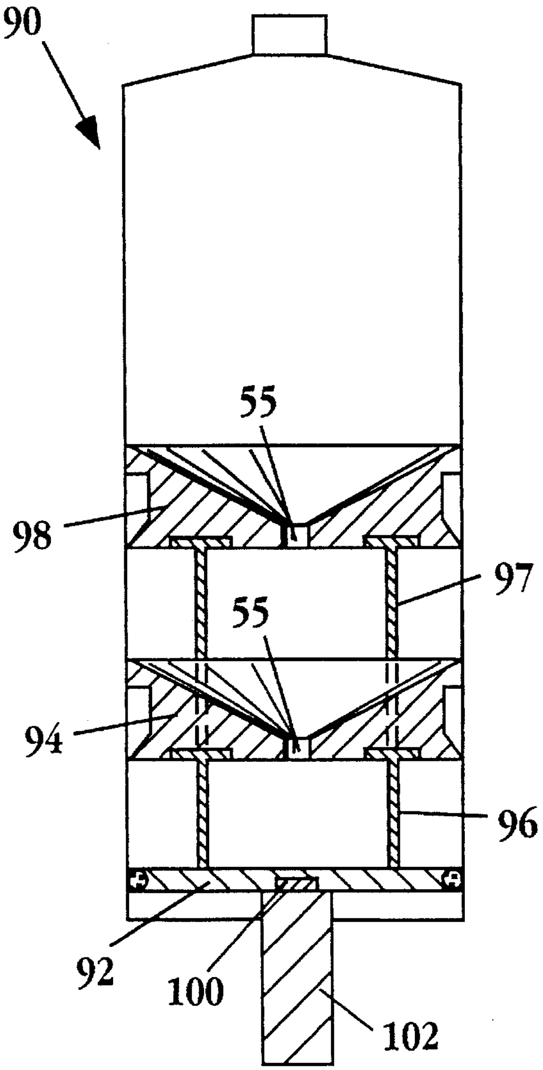
FIG. 11 is a cross-sectional view of an alternative embodiment of the centrifuge syringe of FIG. 5.

FIG. 11 illustrates a further alternative embodiment of the centrifuge syringe of FIG. 5 with an additional constriction member. Dual constriction syringe 90 has a bottom plate 92 connected to a first constriction member 94 by fittings 96. Second constriction member 98 is located above first constriction member 94 to create more compartments to allow separation of cells of differing densities. Second fittings 97 may be used to secure second constriction member 98. Additional constriction members could also be added if a sample of several different densities is to be separated.

FIG. 11 also illustrates one embodiment of the removable and reattachable connection means between the handle 102 and the bottom plate 92. In this embodiment, an internal screw 100 is used, so that the handle 102 can be removed and then reattached after centrifugation.

Preferably, the centrifugation syringe according to the present invention would be provided as a sterilized complete unit with the density gradient material already in place to an appropriate level. In this way, sterility of the syringe is guaranteed and the user need only open the sterile packaging to use the invention. Alternatively, the syringe can be provided in kit form with the density gradient solution separately provided and the needle and handle disattached. The user would then fill the plunger of the syringe with density gradient material, and then assemble the needle and handle before use.

EXAMPLE

Method of isolating $CD34^+$ progenitor hematopoietic cells

The centrifuge syringe and the method of the invention can be used to isolate $CD34^+$ progenitor cells from patients treated with chemotherapy and granulocyte colony stimulating factor (G-CSF) as described below. These cells can then be used to repopulate the patient's lymphohematopoietic system.

Human peripheral blood mononuclear cells (PBMC) are obtained by apheresis of patients treated with daily injections of G-CSF (10 μg/kg/day). Samples are then processed according to standard methods understood by persons skilled in the art.

Cells are resuspended in 25 ml of calcium-free, magnesium-free PBS and then drawn into the syringe on top of 15 ml of PERCOLL™ solution in a 50 ml conical centrifuge syringe fitted with a plunger containing a constriction member, as illustrated in FIG. 1. This PERCOLL™ solution has a density of 1.062 g/ml (osmolality 280±5 mOsm/kg $H_2O$; pH 7.4). The diameter of the opening in the construction member of the syringe preferably is about 0.5 cm. This volume of PERCOLL™ shall be sufficient volume to fill the container to a level higher than about 1 mm above the constriction member. After the sample is drawn in, the needle and plunger are detached. The centrifuge syringe is then centrifuged at about 850 g's for 30 minutes at room temperature. The upper fraction containing $CD34_2+$ cells is collected by ejecting the sample into a sterile container.

I claim:

1. A centrifuge syringe, comprising:

a container with a first end and a second end, said first end comprising a central orifice adapted with a fitting to provide a sterile connection for fluid flow therethrough and said second end defining a central orifice;

a plunger slideably positioned within said container, said plunger defining within said plunger a liquid-material receiving chamber having a single opening region defined by an upper constriction member, wherein said constriction member is positioned and constructed to receive liquid and to retain liquid in said liquid-material receiving chamber, when the plunger is inverted; and an elongated member secured to the lower portion of said plunger and passing through the central orifice of the second end of said container to move the plunger within said container for drawing a fluid sample through said sterile connection.

2. The centrifuge syringe of claim 1, further comprising density gradient material disposed within said liquid-material receiving chamber and extending to a level above said constriction member in the container.

3. The centrifuge syringe of claim 1, wherein said elongated member comprises a substantially rigid handle removably secured to the lower portion of said plunger.

4. The centrifuge syringe of claim 1, further comprising a hollow needle secured to the sterile connection for flow of a fluid sample therethrough.

5. The centrifuge syringe of claim 1, further comprising a sterlizable tubing secured to the sterile connection for flow of a fluid sample therethrough, said tubing being adapted for communication with a sterile fluid sample container.

6. The centrifuge syringe of claim 1 wherein said plunger includes a cylindrical housing that has an outer diameter which sealingly engages with the inner diameter of said container.

7. The centrifuge syringe of claim 6 wherein the cylindrical housing has a variable outer diameter which contacts the inner diameter of said container at the top and the bottom of the plunger.

8. The centrifuge syringe of claim 3 wherein said handle removably and reattachably connects to said plunger through screw means.

9. The centrifuge syringe of claim 1 wherein the opening in the constriction member is round.

10. The centrifuge syringe of claim 1 wherein the opening in the constriction member is oval.

11. The centrifuge syringe of claim 1 wherein the opening in the constriction member is rectangular.

12. The centrifuge syringe of claim 1 wherein the opening in the constriction member is star-shaped.

13. The centrifuge syringe of claim 1 wherein said opening is covered by a grid or mesh.

14. The centrifuge syringe of claim 1 wherein the lower portion of the plunger is a flat plate.

15. The centrifuge syringe of claim 14 wherein the plate is connected to the constriction member by a plurality of fittings.

16. The centrifuge syringe of claim 14 wherein the plate is manufactured of medical grade plastic.

17. The centrifuge syringe of claim 14 wherein the plate further comprises a circumferential seal to seal against the inner diameter of the container.

18. The centrifuge syringe of claim 14 wherein the constriction member is manufactured of silicone or rubber.

19. The centrifuge syringe of claim 2 wherein the density gradient material is selected from the group consisting of PERCOLL™, FICOLL™, Albumin, Cesium Chloride, dextran, sucrose and METRIZOATE™.

20. A closed system for centrifugation analysis of fluid, comprising:

a fluid sample container;

tubing connected to and communicating with said container for flow of fluid therethrough;

a centrifugation syringe connected to and communicating with said tubing for drawing a fluid sample from said container, said syringe comprising an outer housing having a first end and a second end, said first end defining an opening with a fitting removably connected to said tubing, said second end defining an opening, a plunger slideably positioned within the outer housing, said plunger defining within said plunger a liquid-material receiving chamber having a single opening region defined by an upper constriction member, wherein said constriction member is positioned and constructed to receive liquid and to retain liquid in said liquid-material receiving chamber, when the plunger is inverted, and an elongated member secured to the lower portion of said plunger and passing through the outer housing second end opening, said elongated member adapted to be pulled out of said housing to pull back the plunger and draw a fluid sample through the tubing from the fluid container.

21. The system of claim 20, further comprising a density gradient material filling the liquid-material receiving chamber of said plunger and extending to a level in said outer housing above the plunger constriction member.

22. The system of claim 20, wherein the plunger includes a cylindrical housing that has an outer diameter which sealingly engages the outer housing with an at least substantially fluid-tight fit.

23. The system of claim 20, wherein said plunger top and bottom portions are secured together by a plurality of individual, elongated fittings.

24. The system of claim 20, wherein said syringe elongated member comprises a substantially rigid handle removably and reattachably secured to the lower portion of said plunger.

25. A centrifugation kit, comprising: at least one centrifuge syringe including an outer housing having a first end and a second end, said first end defining an opening adapted to provide a sterile connection for fluid flow therethrough, said second end defining an opening, and a plunger slideably positioned within the outer housing, said plunger defining within said plunger a liquid material receiving chamber having a single opening region defined by an upper constriction member, wherein said constriction member is positioned and constructed to receive liquid and to retain liquid in said liquid-material receiving chamber, when the plunger is inverted;

a handle adapted to be secured to the lower portion of said plunger and pass through the outer housing second end opening to be pulled out of said housing to pull back the plunger and draw a fluid sample through said sterile connection; and a quantity of density gradient material sufficient to fill the liquid-material receiving chamber in the plunger and extend to a level in the outer housing above said constriction member.

26. The kit of claim 25, wherein the quantity of density gradient material is at least sufficient to fill the outer housing to a level at least about 1 mm above said constriction member.

27. The kit of claim 26, further comprising a hollow needle adapted to be mounted on the sterile fitting for flow of fluid therethrough.

28. The kit of claim 26, further comprising tubing adapted to be connected to the sterile fitting for flow of fluid therethrough.

29. The kit of claim 28, further comprising a fluid sample container adapted to connected be to the tubing for fluid communication between said container and the centrifuge syringe.

30. A method of extracting and centrifuging a fluid specimen utilizing a syringe including an outer container with an inner plunger, said plunger defining within said plunger a liquid-material receiving chamber having a single opening region defined by an upper constriction member, wherein said constriction member is positioned and constructed to receive liquid and to retain liquid in said liquid-material receiving chamber, when the plunger is inverted, and where the lower portion of the plunger is connected to a handle, comprising the steps of:

filling said liquid-material chamber and syringe with a density gradient material to a level above said constriction member;

drawing a sample into the container and on top of the density gradient material by pulling said handle;

removing the handle from the plunger;

placing the syringe in a centrifuge;

applying centrifugal force to said syringe; and removing at least a part of said sample remaining above the annular member after applying centrifugal force.

31. The method of claim 30, wherein said step applying centrifugal force forms at least two layers of different density above the constriction member and said removing step comprises removing the part of said sample having greater density.

32. The method of claim 30, wherein the syringe includes a needle communicating with the container and the drawing step comprises drawing the sample through the needle directly from a patient.

33. The method of claim 32, wherein the step of removing the sample comprises pouring off the sample from the syringe through an orifice from which the needle was removed.

34. The method of claim 30, wherein said drawing step includes connecting the syringe to a sample container for fluid communication therebetween; drawing a sample from the sample container into the syringe container; and removing the connection to the sample container.

35. The method of claim 30, wherein the step of removing the sample comprises reattaching the handle of said plunger and pushing said handle and plunger into said syringe to force said sample from said syringe.

* * * * *